United States Patent [19]

Greco et al.

[11] Patent Number: 4,988,800

[45] Date of Patent: Jan. 29, 1991

[54] PREPARATION OF RARE EARTH ALKOXIDES USING CATALYST

[75] Inventors: Carl C. Greco, Garnerville; Johst H. Burk, Mohegan Lake, both of N.Y.

[73] Assignee: Akzo America Inc., New York, N.Y.

[21] Appl. No.: 200,484

[22] Filed: May 31, 1988

[51] Int. Cl.$^5$ ................................................ C07F 5/00
[52] U.S. Cl. ..................................... 534/15; 505/734; 502/171
[58] Field of Search .......................................... 534/15

[56] References Cited

U.S. PATENT DOCUMENTS

| | | | |
|---|---|---|---|
| 3,278,571 | 10/1966 | Mazdiyasni et al. | 534/15 |
| 3,356,703 | 12/1967 | Mazdiyasni et al. | 534/15 |
| 3,757,412 | 9/1973 | Mazdiyasni et al. | 534/15 |
| 4,720,474 | 1/1988 | Vasilevskis et al. | 502/165 |

OTHER PUBLICATIONS

Inorganic Chemistry, vol. 5 (1965), pp. 342–346.
Inorganic Chemistry, vol. 9 (1970), pp. 2783–2787.

*Primary Examiner*—Patrick P. Garvin
*Attorney, Agent, or Firm*—Richard P. Fennelly; Louis A. Morris

[57] ABSTRACT

The reaction of rare earth metals and alcohols, to form rare earth alkoxides, is catalyzed by the use of an inorganic, halide-free mercury salt (e.g., mercury nitrate or mercury sulfate).

8 Claims, No Drawings

PREPARATION OF RARE EARTH ALKOXIDES USING CATALYST

BACKGROUND OF THE INVENTION

1. Field of the Invention

The present invention relates to a catalytic process for the manufacture of rare earth alkoxides.

2. Description of the prior Art

A number of prior art references speak of the preparation of rare earth alkoxides using halide-containing mercury compounds or mixtures containing them as catalysts. For example, U.S. Pat. No. 3,278,571 mentions the use of mercuric chloride as a catalyst, and U.S. patent No. 3,757,412 mentions the use of mercuric iodide or a mixture of mercuric chloride and mercuric acetate. Certain literature (non-patent) references also mention the use of halide-containing mercury compounds as catalytic agents in the formation of rare earth alkoxides by reaction of an alcohol and the rare earth metal. Inorganic Chemistry, Vol. 5 (1965) pp. 342–346 discloses mercuric chloride as a catalyst for such a reaction and Inorganic Chemistry, Vol. 9 (1970) pp. 2788–2787 also mentions the use of mercuric chloride.

In the above disclosures, a mercury chloride catalyst figures prominently. However, recent work in regard to formulation of rare earth oxide-containing ceramic materials renders it highly undesirable to use a halide-containing (e.g., chloride-containing) catalyst. In those instances where the ultimate ceramic is intended for structural end use applications, the use of a chloride-containing catalyst can introduce unwanted chloride anion contamination into the final material bringing about undesired defects in the crystal lattice to the material thereby weakening it. In ceramic applications where electrical conductivity is the desired result (e.g., in metal oxide superconductors) the chloride anion impurity can undesirably alter the conductivity performance of the material.

Chloride anion impurities in the final ceramic material are substantially intractable and easy means for their removal have not been devised. Hence, there are major deficiencies in the previously described methods for forming rare earth alkoxides in accordance With a number of current programs to make ceramic materials with structural or electrical end use applications. It is to this shortcoming of these prior art procedures that the instant invention is directed.

SUMMARY OF THE PRESENT INVENTION

The present invention relates to the preparation of rare earth alkoxides without the use of a halide-containing mercury compound as a catalyst. The present process relies upon the use of a non-halide. inorganic mercury salt as a catalyst for the reaction of a rare earth and an alcohol to form the desired rare earth alkoxide. The instant process insures a substantially halide-free rare earth alkoxide which can be further processed via sol-gel techniques and pyrolysis to ultimately achieve metal oxide-based ceramics substantially free of halide ion contamination as desired by the art.

DETAILED DESCRIPTION OF THE PRESENT INVENTION

The present process is directed to the preparation of rare earth alkoxides by the reaction of a rare earth metal with an appropriate alcohol. The rare earth metals contemplated by the instant invention include those of the lanthanum series (Atomic Nos. 57–71) as well as the element yttrium.

The type of alcohols which can be reacted with the foregoing rare earth metals are also known to persons of ordinary skill in the art and include the straight and branched aliphatic alcohols including isopropanol, methoxypropanol, and the like. Generally speaking, the carbon chain length of the alkyl group of such alcohols can range anywhere from about 1 to about 10 carbon atoms.

The molar ratio of rare earth metal to alcohol which can be used in accordance with the present invention can range from about 1:3 to about 1:6, in accordance with conventional practice. The reaction can be conducted at temperatures ranging from about 80° C. to about 150° C.

The present invention includes, as an essential element, the use of an inorganic, halide-free mercury salt to catalyze the reaction of the rare earth metal and the alcohol. The mercury salts that are used in accordance with the present invention have divalent anions derived from strong mineral acids such as sulfuric acid and nitric acid. Representative mercury salt catalysts for use in regard to the present invention include mercury (II) sulfate and mercury (II) nitrate. Generally speaking, the catalytic amount of the mercury catalyst which is utilized. In accordance with the present invention, can range up to about 1%. e.g., from about 0.1% to about 1.0%, by weight of the reactants.

The present invention allows for the preparation of metal alkoxides, in good yield, which are substantially free of undesired halide contamination thereby allowing the synthesis of metal oxide-based ceramics also free of such contamination.

The foregoing invention is further illustrated by the following Examples.

EXAMPLE 1

To a 1-liter, 3-neck flask was added 30 grams of lanthanum shavings and 600 cc of fresh, dry methoxy propanol. To this was also added 0.5 grams of mercury (II) sulfate. The resulting mixture was heated to reflux during which there was a constant evolution of hydrogen for at least 10 hours. The mixture was heated at reflux for a total time of 18 hours and then allowed to cool to room temperature. The reaction mixture was filtered through diatomaceous earth (CELITE brand) using an air-less filtering flask. The filtrate was collected and distilled at reduced pressure (30–50 mm of Hg) and at a pot temperature of 60°–80°C. to remove the excess alcohol. A viscous oil remained as the product lanthanum methoxypropoxide. yield: 83 grams (Theory: 87.6), 95% yield.

EXAMPLE 2

The same reaction was done as in Example 1 with the exception that 0.5 grams of mercury (II) nitrate Was used as the catalyst. The percent yield of lanthanum methoxypropoxide was 91% of theory.

EXAMPLE 3

The same procedure was used as described in Example 1, except that 50 grams of yttrium shavings were used instead of lanthanum shavings. The alcohol used in this example was isopropanol (600 cc) and the yield of yttrium isopropoxide was 65% of theory.

EXAMPLE 4

To a 1-liter, 3-neck flask was added 35 grams of lanthanum shavings and 600 cc of fresh, dry isopropanol. To this was added 0.5 grams of mercury (II) sulfate. The resulting mixture was refluxed for 48 hours, during which hydrogen was evolved. The excess alcohol was distilled off until 450 cc was collected. About 600 cc of toluene was added to the liquid distillation residue, the resulting solution was heated to 100° C. and then filtered through diatomaceous earth (CELITE brand) using an air-less filtering flask. The filtrate was distilled at reduced pressure to remove the solvent. A solid remained as the product in only 9 grams. The remainder of the product was on the filter. The solubility of the product was only about 1–2% in toluene. The product was collected from the filter cake by dissolving in 500 cc of methoxypropanol. The yield of product, lanthanum isopropoxide, was 69 grams, total, which represents a 88% yield.

The foregoing Examples have been presented to illustrate certain preferred embodiments of the present invention and should not be construed in a limiting sense. The scope of protection that is sought is set forth in the claims which follow.

We claim:

1. A catalytic process for the manufacture of rare earth alkoxides by the reaction of a rare earth metal and an alcohol in the presence of a catalytically effective amount of an inorganic, halide-free mercury salt for the reaction.

2. A process as claimed in claim 1 wherein the mercury salt comprises a divalent anion derived from a strong mineral acid.

3. A process as claimed in claim 2 wherein the mercury salt is present at from about 0.1% to about 1.0% by weight of the reactants.

4. A process as claimed in claim 1 wherein the mercury salt is mercury (II) sulfate.

5. A process as claimed in claim 1 wherein the mercury salt is mercury (II) nitrate.

6. A process as claimed in claim 1 wherein the mercury salt comprises a divalent anion derived from a strong mineral acid and is present at from about 0.1% to about 1.0% by weight of the reactants and the mole ratio of rare earth metal to alcohol is from about 1:3 to about 1:6.

7. A process as claimed in claim 6 wherein the mercury salt is mercury (II) sulfate.

8. A process as claimed in claim 6 wherein the mercury salt is mercury (II) nitrate.

* * * * *